United States Patent
Hu et al.

(10) Patent No.: US 10,287,549 B2
(45) Date of Patent: May 14, 2019

(54) MUSCLE STEM CELL IN VITRO CULTURE METHOD AND APPLICATION

(71) Applicant: SHANGHAI INSTITUTES FOR BIOLOGICAL SCIENCES, CHINESE ACADEMY OF SCIENCES, Shanghai (CN)

(72) Inventors: Ping Hu, Shanghai (CN); Xin Fu, Shanghai (CN); Jun Xiao, Shanghai (CN)

(73) Assignee: Shanghai Institutes for Biological Sciences, Chinese Academy of Sciences, Shanghai (CN)

( * ) Notice: Subject to any disclaimer, the term of this patent is extended or adjusted under 35 U.S.C. 154(b) by 593 days.

(21) Appl. No.: 14/894,642

(22) PCT Filed: May 21, 2014

(86) PCT No.: PCT/CN2014/077952
§ 371 (c)(1),
(2) Date: Mar. 14, 2016

(87) PCT Pub. No.: WO2014/190866
PCT Pub. Date: Dec. 4, 2014

(65) Prior Publication Data
US 2016/0177266 A1    Jun. 23, 2016

(30) Foreign Application Priority Data

May 29, 2013 (CN) .......................... 2013 1 0205059

(51) Int. Cl.
C12N 5/077 (2010.01)
A61K 35/34 (2015.01)

(52) U.S. Cl.
CPC ............ *C12N 5/0659* (2013.01); *A61K 35/34* (2013.01); *C12N 2501/20* (2013.01); *C12N 2501/21* (2013.01); *C12N 2501/22* (2013.01); *C12N 2501/2301* (2013.01); *C12N 2501/231* (2013.01); *C12N 2501/2303* (2013.01); *C12N 2501/2313* (2013.01); *C12N 2501/2316* (2013.01); *C12N 2501/2317* (2013.01); *C12N 2501/24* (2013.01); *C12N 2501/25* (2013.01); *C12N 2502/1114* (2013.01)

(58) Field of Classification Search
CPC .......... C12N 5/0659; C12N 2502/1114; C12N 2501/2317; C12N 2501/2316; C12N 2501/2313; C12N 2501/231; C12N 2501/2303; C12N 2501/25; C12N 2501/22; C12N 2501/21; C12N 2501/20; C12N 2501/24; C12N 2501/2301; A61K 35/34

See application file for complete search history.

(56) References Cited

U.S. PATENT DOCUMENTS 5,143,842 A    9/1992 Ham et al.
2001/0026937 A1 * 10/2001 Punnonen et al. ............ 435/366
2008/0292641 A1 * 11/2008 Sass et al. ................. 424/172.1

FOREIGN PATENT DOCUMENTS

CN    102140438 A    8/2011
JP    2004-536139 A    12/2004
JP    2007-202435 A    8/2007

OTHER PUBLICATIONS

Siegel A. L. et al., "Muscle satellite cell proliferation and association: new insights from myofiber time-lapse imaging", Skeletal Muscle, Feb. 2, 2011, vol. 1, No. 1, pp. 1-7 (doi:10.1186/2044-5040-1-7). (Year: 2011).*
Ayache S. et al., "Comparison of proteomic profiles of serum, plasma, and modified media supplements used for cell culture and expansion", Journal of Translational Medicine, 2006, vol. 4/1/40, total pp. 1-12. (Year: 2006).*
Lund F. E., "Cytokine-producing B lymphocytes—key regulators of immunity", Curr. Opin. Immunol., Jun. 2008, vol. 20, No. 3, pp. 332-338 (total pp. 1-11). (Year: 2008).*
Wang D. et al., "Proteomic Profiling of Bone Marrow Mesenchymal Stem Cells upon Transforming Growth Factor beta-1 Stimulation", The Journal of Biological Chemistry, Oct. 15, 2004, vol. 279, No. 42, pp. 43725-43734. (Year: 2004).*
Deasy B.M. et al., "Mechanisms of Muscle Stem Cell Expansion with Cytokines", Stem Cells, 2002, vol. 20, pp. 50-60 (Year: 2002).*
U'-Lesault P-F. et al., "Macrophages Improve Survival, Proliferation and Migration of Engrafted Myogenic Precursor Cells into MDX Skeletal Muscle", PLOS One, Oct. 2012, vol. 7, No. 10, e46698, total pp. 1-10. (Year: 2012).*
Li, Weiyin, et al., "Combined Effect of bFGF and TGF-beta on the Proliferation of Rat Skeletal Muscle Satellite Cells in Vitro", Medical Journal of Wuhan University, vol. 28, No. 26, Nov. 2007, pp. 733-736.
Wang, Xiao-ling, et al., "Effects of Angelica Polysaccharides on the Proliferation of Mouse Skeletal Satellite Cells and the Expression of Stem Cell Factor Receptor Protein", CJITWM, vol. 32, No. 1, Jan. 2012, pp. 93-96.

(Continued)

*Primary Examiner* — Satyendra K Singh
(74) *Attorney, Agent, or Firm* — Banner & Witcoff, Ltd.; John P. Iwanicki

(57) ABSTRACT

Provided is a muscle stem cell in vitro culture method. A muscle stem cell is cultivated in vitro by using a cell culture medium of a cell factor added with a blood cell or a conditioned medium of the blood cell. Also provided is a culture medium used in the muscle stem cell in vitro culture method and an application thereof.

5 Claims, 3 Drawing Sheets

(56) References Cited

OTHER PUBLICATIONS

Rando, T. A., et al., "Primary Mouse Myoblast Purification, Characterization, and Transplantation for Cell-mediated Gene Therapy", The Journal of Cell Biology, vol. 125, No. 6, Jun. 1994, pp. 1275-1287.

Gilbert, P.M., et al., "Substrate Elasticity Regulates Skeletal Muscle Stem Cell Self-Renewal in Culture", Science, vol. 329, Aug. 27, 2010, pp. 1078-1081.

* cited by examiner

MUSCLE STEM CELL IN VITRO CULTURE METHOD AND APPLICATION

RELATED APPLICATION

This application is a national phase entry under 35 USC 371 of International Patent Application No.: PCT/CN2014/077952 filed on 21 May 2014, which claims priority from Chinese Application No. 201310205059.X filed on 29 May 2013, the disclosure of which is incorporated in their entirety by reference herein.

TECHNICAL FIELD

This disclosure belongs to the field of biotechnology and medical science, more particularly to the field of muscle stem cell related cell culture and cell therapy.

BACKGROUND ART

Muscle stem cells are responsible for the postnatal muscle mass gain and muscle regeneration. Muscle stem cells are non-tumorigenic in vivo. The application of muscle stem cells have no ethical problems faced by embryonic stem cells. They therefore display wide application prospects to treat various muscle degenerative diseases such as muscle wasting and dystrophy etc. One of the major obstacles preventing the application of muscle stem cells in clinic is the lack of method to support long term muscle stem cell culturing in vitro. Similar to the majority of adult stem cells, muscle stem cells can only divide for 2-4 times in the in vitro culturing system and can hardly be serially expanded.

The current protocols to culture muscle stem cells (satellite cells) are largely all based on the method established by Dr. Bischoff in 1986. The method was further optimized by Dr. Beauchamp et al. and it cultures muscle stem cells in F10 basal culture medium supplemented with 10 ng/ml FGF. Under this culture condition, muscle stem cells can divide 3-5 times. When muscle stem cells are continuously expanded, they will go through a major crisis. During the major crisis, most of the cells die. The survived cells differentiate to progenitor cells losing the stemness. Therefore, after culturing in vitro for 1-3 passages (3-12 days), all the isolated muscle stem cells differentiate to progenitor cells losing the stemness. And the molecular markers of muscle stem cell cannot be detected in these progenitor cells. These progenitor cells show very low efficiency to repair muscle injury in vivo. They are unable to form functional stem cells in vivo after injury reparation and fail to repair secondary injury after transplantation. (Bischoff P. *A satellite cell mitogen from crushed adult muscle. Dev Biol.*, 1986. 115(1): 140-147. Beauchamp, J R, et al., *Expression of CD34 and Myf5 defines the majority of quiescent adult skeletal muscle satellite cells. J Cell Biol.* 2000. 1546): p. 1221-34.) That is, the muscle stem cells will go through a crisis phase if the current in vitro culturing system of muscle stem cells is applied. After the crisis, the majority of the cells with the ability to proliferate have become muscle progenitor cells and lose the ability to repair muscle injury in vivo. Due to the presence of the said problem, the genetic correction in muscle stem cells to treat muscle degenerative diseases is difficult to be applied in clinic.

CONTENTS OF THE INVENTION

The present disclosure aims at overcoming the defectiveness in the art and providing a muscle stem cells medium and the usages thereof.

In the first aspect of the present disclosure, provided is a method for culturing muscle stem cells in vitro, comprising culture the muscle stem cells in cell medium supplemented with cytokines secreted by blood cells or conditional medium of blood cells in vitro. The method for culturing muscle stem cells in vitro of this disclosure is applied to culture muscle stem cells in vitro for a long term.

In the second aspect of the present disclosure, provided is a medium for culturing muscle stem cells, which is cell medium supplemented with cytokines secreted by blood cells or conditional medium of blood cells.

All the cytokines secreted by blood cells supplemented to said cell medium supplemented with cytokines secreted by blood cells, the blood cells used to prepare said conditional medium of blood cells are from the same species as the muscle stem cells to be cultured.

When muscle stem cells are cultured in medium added with animal serum, the cytokines originally exists in the animal serum are not included in said cytokines secreted by blood cells supplemented to said cell medium supplemented with cytokines secreted by blood cells.

The cell culturing medium supplemented with cytokines secreted by blood cells can be made by addition of cytokines secreted by blood cells to general cell culturing medium.

Further, said blood cell conditional medium is lymphocyte conditional medium, more preferably, is B cell conditional medium or T cell conditional medium.

Said cytokines secreted by blood cells are various cytokines selected from the following group: GM-CSF (Granulocyte-macrophage colony-stimulating factor), sICAM-1 (human soluble Intercellular adhesion molecule), IFN gamma (Interferon gamma), IL1 (interleukin 1), IL-1 alpha receptor (Interleukin 1 alpha receptor), IL1 alpha (Interleukin 1 alpha), IL-3 (Interleukin 3), IL2 (Interleukin 2), IL-10 (Interleukin 10), IL-16 (Interleukin 16), IL13 (Interleukin 13), IL-17 (Interleukin 17), IP-10 (Interferon-inducible Protein 10), SCYA2 (Small Inducible Cytokine A2), MIG (Interferon gamma induced monokines), MIP-1 alpha (Macrophage inflammatory protein-1 alpha), TGF-beta (Transforming growth factor beta), IL-4 (Interleukin 4), TRAF6 (TNF receptor related factor 6), FGF (Fibroblast growth factors), IGF (Insulin-like growth factor 1), PDGF (Platelet derived growth factor), LIF (Leukemia inhibitory factor), mTOR (mammalian target of rapamycin), LPS (Lipopolysaccharide), TLR1 (Toll-like receptor 1), IL12 (Interleukin 12), IL23 (Interleukin 23), NGF (Nerve growth factor), TNF alpha (alpha interferon) and IL1 beta (Interleukin 1 beta).

In said cell medium supplemented with cytokines secreted by blood cells or conditional medium of blood cells, the total concentration of cytokines secreted by blood cells supplemented should be no less than 6 ng/ml, preferably 50-4500 ng/ml.

Furthermore, in said cell medium supplemented with cytokines secreted by blood cells or conditional medium of blood cells, the concentration of any individual cytokine supplemented should be greater than 0.5 ng/ml, preferably greater than 1 ng/ml, more preferably greater than 10 ng/ml, more preferably greater than 25 ng/ml, more preferably greater 50 ng/ml.

Furthermore, said cytokines secreted by blood cells being supplemented should at least contain IL1, IL4, IL13, TNF alpha, IL2 and IFN gamma.

Furthermore, in said cell medium supplemented with cytokines secreted by blood cells or conditional medium of blood cells, the total concentration of the IL1, IL4, IL13, TNF alpha, IL2 and IFN gamma should be no less than 6 ng/ml, preferably 50-1250 ng/ml.

Furthermore, in said cell medium supplemented with cytokines secreted by blood cells or conditional medium of blood cells, any individual cytokine among the group IL1, IL4, IL13, TNF alpha, IL2 and IFN gamma should be no less than 0.5 ng/ml, preferably higher than 1 ng/ml, more preferably higher than 10 ng/ml; usually, 50-500 ng/ml is optional.

In the third aspect of the present disclosure, provided is use of the above cytokines secreted by blood cells or conditional medium of blood cells for culturing muscle stem cells in vitro.

The cytokines secreted by blood cells or conditional medium of blood cells can promote the proliferation of muscle stem cells in vitro and maintain the stemness thereof.

In the fourth aspect of the present disclosure, provided is a preparation for treating muscle degenerative diseases, the main active component of which is the muscle stem cells cultured by any of the method for culturing muscle stem cells in vitro in this disclosure.

Specifically, the main active component of the preparation is the autologous muscle stem cells obtained from the patient and cultured by the method for culturing muscle stem cells in vitro of this disclosure.

More specifically, the preparation can be an injection, a surgery implant agent.

The preparation usually contains common pharmaceutical excipients.

In the fifth aspect of the present disclosure, provided is a cell therapy method for muscle degenerative diseases of patient, comprising the following steps:

1) Collect muscle stem cells of patient;
2) Expand the muscle stem cells collected in step 1) using the muscle stem cells medium described in this disclosure in vitro to obtain sufficient number of muscle stem cells;
3) Administrate the obtained muscle stem cells to the injury part of patient.

Wherein, the drug administration in step 3) can be injection administration, the muscle stem cells are administrated to the muscle injury part by muscular injection.

The amplified muscle stem cells can be trypsinized from culturing dishes. The digested cells are resuspended in physiological saline to obtain the muscle stem cells injection.

Using the method for culturing and passaging muscle stem cells in vitro described in this disclosure, muscle stem cells can be amplified to a large number and maintain their stemness, the number of the stem cells for regenerative medicine therapy is greatly improved. It is become possible to isolate muscle stem cells from a small biopsy of the patient, gene correct and expand in vitro, inject the muscle stem cells containing corrected genetic informations to body for cell therapy, thus treat various genetic muscle degenerative diseases.

The current available method to culture muscle stem cells cannot support long term culture of muscle stem cells with differentiation potential in vitro, and cannot be passaged. If muscle stem cells are cultured for more than 12 days in vitro, all the cells will differentiate to progenitor cells and lose the ability to repair muscle injury in vivo. Under the current culturing conditions, muscle stem cells can only divide 3-5 times, the cells can be amplified for at most 32 fold as compared with the number of original cells, after that the cells lose their ability to division. In order to obtain sufficient number of muscle stem cells for therapy, a big chunk of muscle tissues shall be taken for isolating and purifying the muscle stem cells, which is not feasible in clinic. In the medium of this disclosure, muscle stem cells can divide more than 10 times, more than 1000 fold of amplification of the original cells can be achieved in every passage. More importantly, the medium described in this disclosure can support serial passage of muscle stem cells as well as maintain their stemness and differentiation potentials. Therefore, the final number of muscle stem cells will be $2^m \times 2^n$ fold of the initial isolated and purified muscle stem cells; m represents the number of division in each passage; n represents the number of passage. m will be at least 12 and n will be at least 40 in the method described in this disclosure. Therefore, the number of the muscle stem cells can be amplified at least $4.5 \times 10^{15}$ folds of the original isolated and purified cells. The expanded muscle stem cells maintain their stemness and complete differentiation potential s. They can repair muscle injury in vivo. After being injected into the mouse, these stem cells can take part in the repair of muscle injury efficiently and supplement the stem cells storage; and they have the ability to repair the secondary injury after transplanted. It is a feasible strategy to obtain a little muscle tissue (in grams) by mini-invasive surgery, isolate and purify a few muscle stem cells, expand these cells in vitro to obtain enough muscle stem cells for regenerative medicine therapy in clinic.

Figure 1:
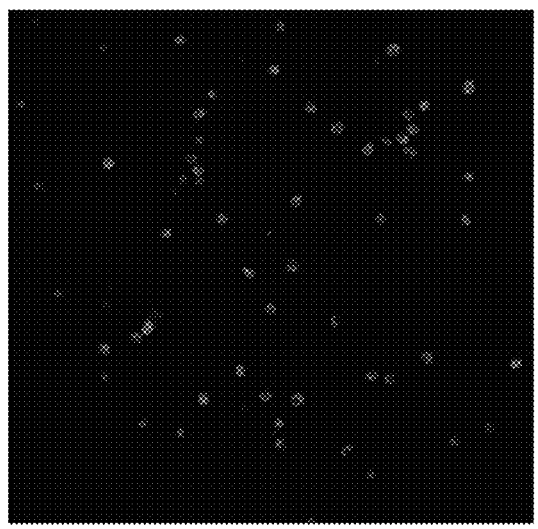
FIG. 1. P0 muscle stem cells cultured in F10 medium supplemented with cytokines (Staining for Pax7).
Figure 2:
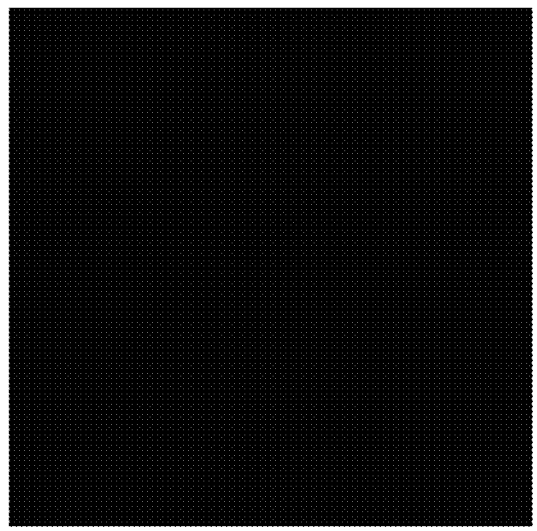
FIG. 2. Fibroblasts (control) cultured in F10 medium supplemented with cytokines (Staining for Pax7).
Figure 3:
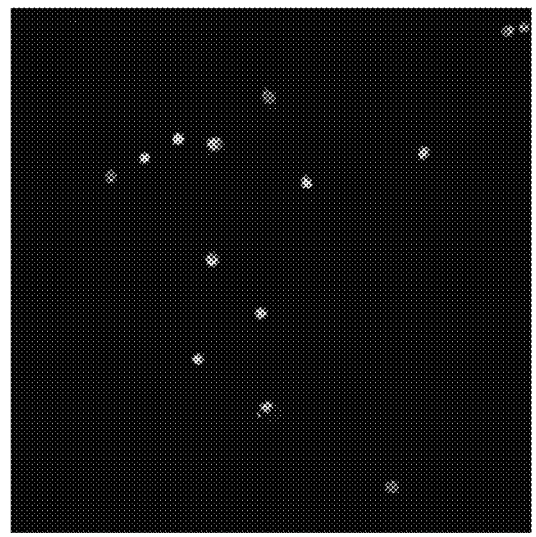
FIG. 3. P8 muscle stein cells cultured in F10 medium supplemented with cytokines (Staining for Pax7).
Figure 4:
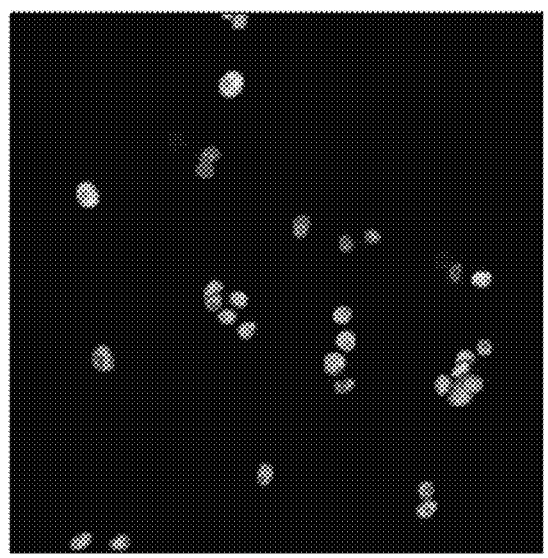
FIG. 4. P22 muscle stem cells cultured in F10 medium supplemented with cytokines (Staining for Pax7).
Figure 5:
FIG. 5. Differentiating potentials of P0 cells cultured in F10 medium supplemented with cytokines.
Figure 6:
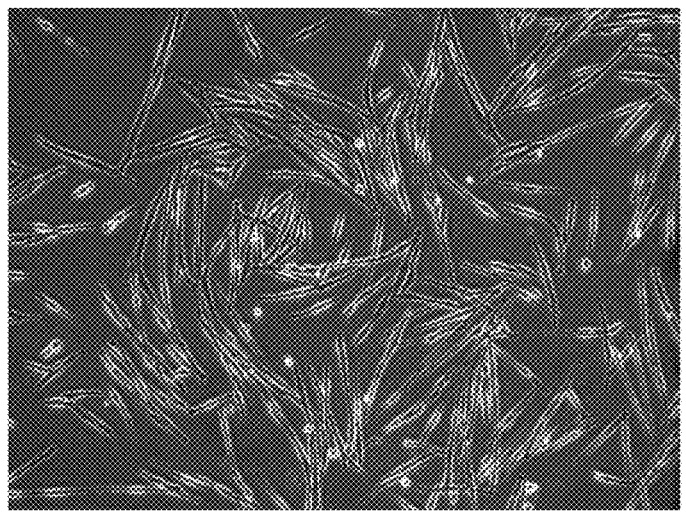
FIG. 6. Differentiating potentials of P22 muscle stem cells cultured in F10 medium supplemented with cytokines.
Figure 7:
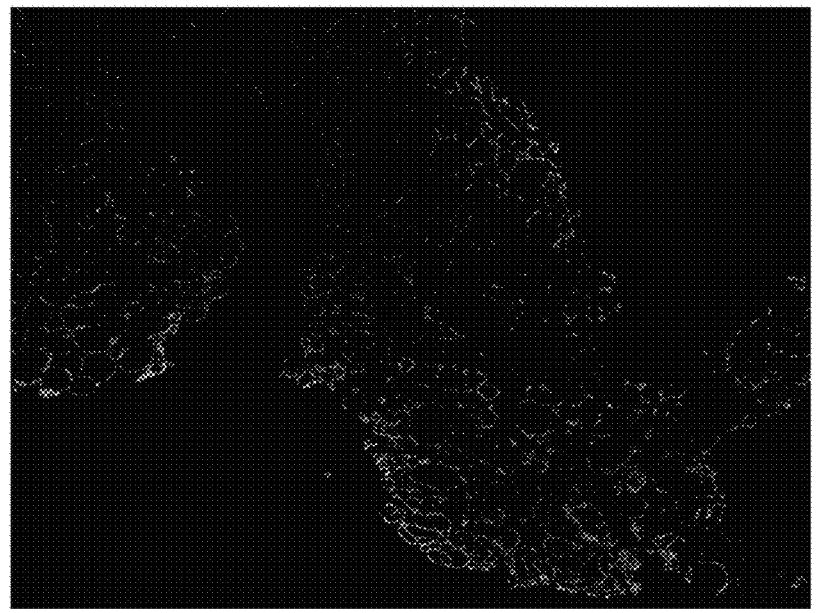
FIG. 7. The result of repair muscle injury in vivo of the muscle stem cells expressing RFP cultured in F10 medium supplemented with cytokines.
Figure 8:
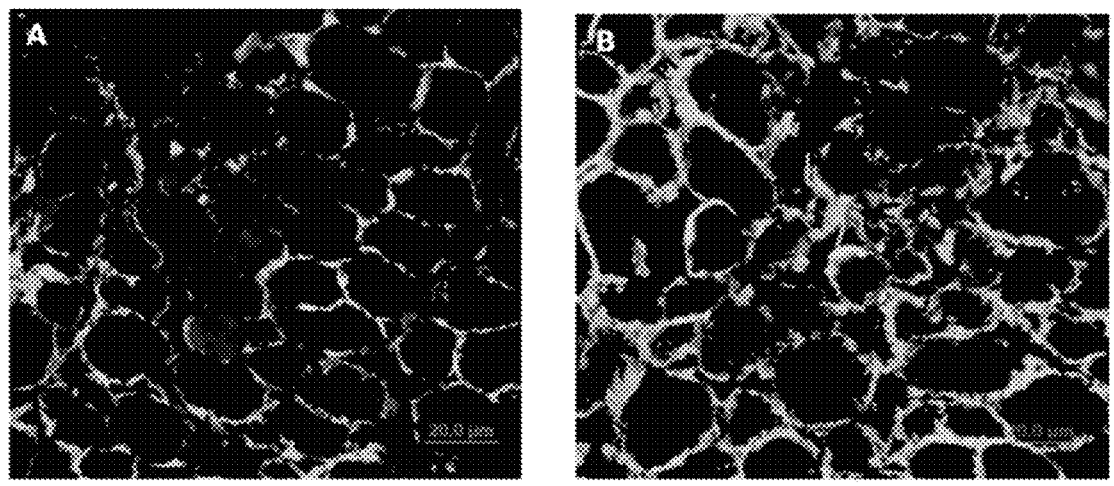
FIG. 8. Muscle stem cells expressing RFP cultured in F10 medium supplemented with cytokines had the abilities to repair muscle injury in vivo. RIP expressing muscle stem cells cultured in vitro were injected into injury muscle with non-fluorescent. Seven days later, the integration of red cells could be detected in the muscle sections. Red myofibers originating from the injected muscle stem cells expressing RFP were formed in the injury part.

A. The reparation efficiency injected with muscle stem cells cultured in medium supplemented with cytokines.

B. The reparation efficiency injected with muscle stem cells cultured in T cell conditional medium.

DESCRIPTION OF THE PREFERRED EMBODIMENTS

This disclosure revealed that co-culturing with blood cells can promote proliferation of muscle stem cells in a cell-cell (blood cell and muscle stem cell) contact independent manner. Blood cell conditional medium can promote the proliferation of muscle stem cells. To be more specific Both B cell and T cell conditional medium can promote the proliferation of muscle stem cells. Muscle stem cells cultured in T cell conditional medium are able to divide more than 10 times at each passage, and these cells can be continuously expanded for over 40 passages in vitro. The cytokines secreted by T cells were identified after a series of isolation and purification steps. The combination of these cytokines can promote the proliferation of muscle stem cells in vitro. Muscle stem cells treated with cytokines express the muscle stem cell molecular markers, display enhanced proliferation abilities, and can be continuously expanded for more than 40 passages. Every passage of muscle stem cells express the molecular markers of muscle stem cells, display enhanced proliferation abilities, and can differentiate to mature myotubes efficiently. More importantly, when these muscle stem cells cultured by T cell conditional medium or cytokines are injected into muscle injury-induced mouse, the injected muscle stem cells are able to repair muscle injury and form new myofibers, indicating that the muscle stem cells obtained in this disclosure are real muscle stem cells.

The method for culturing muscle cells in vitro of this disclosure is to culture muscle stem cells in cell medium supplemented with cytokines secreted by blood cells or conditional medium of blood cells in vitro.

The key of this disclosure is to improve the culture medium for culturing muscle stem cells in vitro. The other aspects for culturing muscle stem cells in vitro are in conformity to the common cell culture.

Best culture condition: Culture in $CO_2$ incubator at 37° C. The preferred $CO_2$ concentration in $CO_2$ incubator is 5% (v/v).

The muscle stem cells are cultured by attachment culture in vitro.

The muscle stem cell medium applied in this disclosure is cell medium supplemented with cytokines secreted by blood cells or blood cell conditional medium.

Cytokines secreted by blood cells supplemented to said cell medium supplemented with cytokines secreted by blood cells should be from the same species as the muscle stem cells to be cultured. Blood cells used to prepare said conditional medium of blood cells are from the same species as the muscle stem cells to be cultured. For example, if mouse muscle stem cells are to be cultured, the cell culture supplemented with cytokines secreted by mouse blood cells or mouse blood cell conditional medium are used; if human muscle stem cells are to be cultured, the cell culture supplemented with cytokines secreted by human blood cells or human blood cell conditional medium are used; and so on.

The "species" is the basic unit of taxonomy. Further, the animal species is selected from mammal. Furthermore, the species is selected Rodentia, Artiodactyla, Perissodactyla, Lagomorpha, Primates et al. of mammals, such as rat, rabbit, sheep, pig, monkey, human et al.

When animal serum is added for cell culture, the cytokines originally existed in the animal serum being added to the medium are not included in said cytokines secreted by blood cells supplemented to said cell medium supplemented with cytokines secreted by blood cells. That is, in this disclosure, when animal serum is added for cell culture, cytokines secreted by blood cells from the same species as muscle stem cells to be cultured must be added separately.

The cell medium supplemented with cytokines secreted by blood cells described in this disclosure is the cell medium not only containing the components for common cell culture, but also supplemented with the cytokines secreted by blood cells.

In the medium for culturing muscle stem cells described in this disclosure, other components and content thereof are in conformity to the common cell culture except for the addition of cytokines secreted by blood cells. The common components of cell culture medium include balanced salt solution, pH regulators, antibiotics, animal serum, essential amino acids for cell growth, vitamins, glucose, pH indicator etc. The balanced salt solution contains the components such as calcium chloride, ferric nitrate, magnesium sulfate, potassium chloride, sodium fluoride, sodium chloride, sodium phosphate, etc. The pH regulators can be 3.7% sodium bicarbonate, HEPES (4-(2-hydroxyethyl)-1-piperazineethanesulfonic acid) solution, sodium pyruvate, etc. The antibiotics can be penicillin, streptomycin, etc. The commonly used animal serum mainly includes bovine serum and horse serum. Vitamins can be choline chloride, folic acid, inositol, niacinamide, calcium pantothenate, pyridoxal hydrochloride, vitamin B6, riboflavin, thiamine, etc.

The cell medium supplemented with cytokines secreted by blood cells can be prepared by addition of the cytokines secreted by blood cells to the commonly used cell culture medium. Wherein, the commonly used cell culture medium can be selected from various common cell cultures such as DMEM, RPMI 1640, MEM, DEME/F12, F10, CD293, medium 231, medium 106. The examples of this disclosure have illustrated the muscle stem cell culture medium added with cytokines secreted by various blood cells in F10 medium.

The blood cell conditional medium refers to the cell medium that blood cells have been cultured in. Specifically, the blood cells are lymphocytes. Most preferably, the blood cells are B cells and/or T cells.

The blood cell conditional medium can be prepared by growing blood cells in the commonly used cell medium followed by removal of the blood cells. B cell conditional medium can be prepared by growing B cells in the commonly used cell medium followed by removal of B cells; T cell conditional medium can be prepared by growing T cells in the commonly used cell medium followed by removal of T cells.

The cytokines secreted by blood cells are various cytokines selected from the following group: GM-CSF, sICAM-1; IFN gamma IL1, IL-1 alpha, IL-1 alpha receptor, IL-3, IL2, IL-10, IL-16, IL13, IL-17, IP-10, SCYA2, MIG, MIP-1 alpha, TGF-beta, IL-4, TRAF6, FGF, IGF, PDGF, LIF, mTOR, LPS, TLR1, IL12, IL23, NGF, TNF alpha, IL1 beta.

All above cytokines can be detected in lymphocyte conditional medium. They are especially enriched in T cell conditional medium.

More preferably, the cytokines secreted by blood cells are at least six cytokines selected from the above cytokines; or the cytokines secreted by blood cells are at least seven cytokines selected from the above cytokines; or the cytokines secreted by blood cells are at least eight cytokines selected from the above cytokines; or the cytokines secreted by blood cells are at least nine cytokines selected from the above cytokines; or the cytokines secreted by blood cells are at least ten cytokines selected from the above cytokines.

In order to maintain the proliferation of muscle stem cells and maintain the stemness of the passaged cells thereof, the total concentration of the cytokines secreted by blood cells can't be too low, generally no less than 6 ng/ml, preferably 50-4500 ng/ml.

The concentration of any individual cytokine secreted by blood cells supplemented to said cell medium supplemented with cytokines secreted by blood cells or conditional medium of blood cells should be greater than 0.5 ng/ml, preferably greater than 1 ng/ml, more preferably greater than 10 ng/ml, usually within the range of 50-500 ng/ml. The description above does not mean that the concentration of the cytokine cannot be higher than 500 ng/ml, but the concentration within the above range is considered to play an active role. It will be no obvious effect if the concentration is too low, and it will lead to waste if the concentration is too high.

Based on experiments, six cytokines secreted by blood cells: IL1, IL4, IL13, TNF alpha, IL2, and IFN gamma have close relationship with proliferation of muscle stem cells and maintaining of stemness thereof. In the preferred embodiment of this disclosure, these six cytokines are required to be supplemented to the medium, and the other cytokines secreted by blood cells can be supplemented optional.

More specifically, the total concentration of the IL1, IL4, IL13, TNF alpha, IL2 and IFN gamma supplemented to said cell medium supplemented with cytokines secreted by blood cells or conditional medium of blood cells should be no less than 6 ng/ml, preferably 50-1250 ng/ml.

More specifically, the concentration of any individual cytokine among the group IL1, IL4, IL13, TNF alpha, IL2 and IFN gamma should be higher than 0.5 ng/ml, preferably higher than 1 ng/ml, more preferably higher than 10 ng/ml; usually, 50-500 ng/ml is optional. If the cytokine concentration is higher than 500 ng/ml, there is no severe side effect on proliferation of muscle stem cells, but the addition of excessive cytokine is unnecessary if the cost is taking into account.

The concentration of cytokines stated above means that in the cell medium supplemented with cytokines secreted by blood cells or conditional medium of blood cells, the final concentration of cytokines secreted by blood cells originated from the same species as the muscle stem cell to be cultured.

This disclosure reveals that cytokines secreted by blood cells or conditional medium of blood cells can be used to culture muscle stem cells in vitro, promote the proliferation of muscle stem cells in vitro and maintain the stemness thereof.

This disclosure also provides a preparation for treating muscle degenerative diseases. The main active component of the preparation is the muscle stem cells cultured by the method for culturing muscle stem cells in vitro of this disclosure.

The main active component of the preparation is the primary muscle stem cells obtained from the patient and cultured by the method for culturing muscle stem cells in vitro of this disclosure.

Based on the experiments of this disclosure, the recommended dosage of administration is about $3 \times 10^6$ muscle stem cells/time. The administration can be single dosage, or can be multiple dosages based on the muscle reparation process of patient. The commonly used administration method is muscular injection. However, that does not mean to exclude other feasible methods in this disclosure.

Commonly, the preparation includes pharmaceutical adjuncts.

The common used pharmaceutical adjuncts include but not limited to: Saline, buffer, glucose, water, glycerol, ethanol, polyols, and the combination thereof. Drug preparation should compatible with the administration method. The preparation described in this disclosure is preferably an injection preparation. For example, saline or solutions containing glucose and other adjuncts can be used to prepare the preparation by conventional method. Other formulation of the preparation can also be prepared by conventional method. The preparation of this disclosure should be prepared under sterilization condition. The preparation described in this disclosure can be used in conjugation with other therapeutic reagents.

This disclosure further provides a method for treating muscle degenerative diseases of patient, including the following steps:

1) Collect muscle stem cells from the patient;

Collection of muscle stem cells of patient: Small muscle biopsy can be obtained from the patient by mini-invasive surgery, followed by the isolation and purification of muscle stem cells from muscle biopsy. The method is well known by the skilled in the art.

2) Expand the muscle stem cells collected in step 1) in vitro using the muscle stem cell medium described in this disclosure to obtain sufficient number of muscle stem cells;

Based on the method for culturing muscle stem cells of this disclosure, after the muscle stem cells are collected from patient, genetic engineering modification, defect gene repair or gene optimization can be performed with the muscle stem cells by known genetic engineering method. The modified muscle stem cells can be further expanded. Therefore, the goal of overcome genetic related muscle disease or mutation related muscle disease, or further optimize muscle tissue is achieved.

3) Apply the obtained muscle stem cells to the muscle injury part of patient.

The muscle stem cells can be injected to the muscle injury part of patient by muscular injection. After injection, the patient should perform regular exercise to improve the integration of muscle stem cells. The repair efficacy can be examined after 4-8 weeks.

Preferred embodiments are given to illustrate the mode of carry out of this disclosure. The skilled in the art can easily understand the other advantages and effects of this disclosure from the description of the specification. This disclosure can be carried out or applied by the other different embodiments. Based on different opinions and applications, various modifications and changes to the details of this specification may be made without departing from the spirit of this disclosure.

unless other declaration, the experimental methods, detection methods, and preparation methods disclosed in this disclosure are all based on the regular technologies in molecular biology, biochemistry, chromatin structure and analysis, analytical chemistry, cell culture, recombinant DNA technology in the art, and regular technologies of related field. These technologies have been extensively described in the current literatures, for detail, the literatures are: Sambrook et al. MOLECULAR CLONING: A LABORATORY MANUAL, Second edition, Cold Spring Harbor Laboratory Press, 1989 and Third edition, 2001; Ausubel et al. CURRENT PROTOCOLS IN MOLECULAR BIOLOGY, John Wiley &, Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, Chromatin (P. M. Wassarman and A. P. Wolffe, eds.), Academic Press, San Diego, 1999; as well as METHODS IN MOLECULAR BIOLOGY, Vol. 119, Chromatin Protocols (P. B. Becker, ed.) Humana Press, Totowa, 1999 etc.

Example 1. Preparation of Mouse T Cell Conditional Medium

Sacrificed the wild type C57/B6 mice and harvested spleens. Wet the spleen with 2-3 ml PBS, milled the spleen, and filtered through 70 μm filter after an appropriate amount of PBS was added, the cell suspension was harvested. Centrifugated at 1000 rpm for 5 minutes, the supernatant was discarded. 5 ml of red cell lysis buffer was added to resuspend the cell. 5 ml of PRMI-1640 medium was added. The cell debris was removed by filtering through a filter mesh. Centrifugated at 1000 rpm for 5 minutes to collect cells. The cells were washed with PRMI-1640 medium twice, the cell density was regulated to $1\times10^9$ cells/L. The cells were seeded to cell culture bottles, ConA was added at a final concentration of 5 mg/L, and incubated at 37° C. in the $CO_2$ incubator for 48 hours, equal volume of PRMI-1640 medium was added and incubated for 24 hours, centrifugated at 3000 rpm for 5 minutes. Transferred the cell supernatant to fresh tubes and stored at −80° C.

The following cytokines were detected in the obtained T cell conditional medium:

Detection method: ELISA detection; see Mouse Cytokine Array, Panel A (Catalog ARY006) from R&D Company.

| Component A | GM-CSF | 200 ng/ml |
| Component B | sICAM-1 | 120 ng/ml |
| Component C | IFN gamma | 160 ng/ml |
| Component D | IL1 | 100 ng/ml |
| Component E | IL-1 alpha receptor | 100 ng/ml |
| Component F | IL-3 | 250 ng/ml |
| Component G | IL2 | 200 ng/ml |
| Component H | IL-10 | 80 ng/ml |
| Component I | IL-16 | 1.30 ng/ml |
| Component J | IL13 | 120 ng/ml |
| Component K | IL-17 | 300 ng/ml |
| Component L | IP-10 | 250 ng/ml |
| Component M | SCYA2 | 80 ng/ml |
| Component N | MIG | 150 ng/ml |
| Component O | MIP-1 alpha | 200 ng/ml |
| Component P | TGF-beta | 150 ng/ml |
| Component Q | IL-4 | 250 ng/ml |
| Component R | TRAF6 | 400 ng/ml |
| Component S | FGF | 25 ng/ml |
| Component T | IGF | 50 ng/ml |
| Component U | PDGF | 80 ng/ml |
| Component V | LIF | 100 ng/ml |
| Component W | IL-1 alpha | 200 ng/ml |
| Component X | mTOR | 30 ng/ml |
| Component Y | LPS | 60 ng/ml |
| Component Z | TLR1 | 55 ng/ml |
| Component Z' | IL12 | 120 ng/ml |
| Component Y' | IL23 | 200 ng/ml |
| Component X' | NGF | 100 ng/ml |
| Component W' | TNFalpha | 100 ng/ml |
| Component V' | IL1 beta | 100 ng/ml |

The concentration of the cytokines present in the T cell conditional medium may vary slightly when use different cell culture or operate by different personnel. However, the variation will not affect the carrying out of this disclosure.

The preparation of human T cell conditional medium was similar to the preparation of mouse T cell conditional medium, except for usage of the human T cells as the culture cells.

The preparation of mouse B cell conditional medium:

Sacrificed the wild type C57/B6 mice and harvested spleens. Wet the spleen with 2-3 ml PBS, milled the spleen, and filtered through 70 μm filter after an appropriate amount of PBS was added, the cell suspension was harvested. Centrifugated at 1000 rpm for 5 minutes, the supernatant was discarded. 5 ml of red cell lysis buffer was added to resuspend the cell. 5 ml of PRMI-1640 medium was added. The cell debris was removed by filtering through a filter mesh. Centrifugated at 1000 rpm for 5 minutes to collect cells. The cells were washed with PRMI-1640 medium twice, the cell density was regulated to $1\times10^9$ cells/L. The cells were seeded to cell culture bottles, LPS was added at a final concentration of 1 mg/L, and incubated at 37° C. in the $CO_2$ incubator for 48 hours, equal volume of PRMI-1640 medium was added and incubated for 24 hours, centrifugated at 3000 rpm for 5 minutes. Transferred the cell supernatant to fresh tubes and stored at −80° C.

The preparation of human B cell conditional medium was similar to the preparation of mouse B cell conditional medium, except for usage of the human B cells.

Preparation of cell culture medium supplemented with cytokines of blood cells:

All the cytokines of blood cells are commercially available.

Protocol to prepare medium supplemented with cytokines of blood cells for culturing muscle stem cells:

The F10 medium powder was dissolved in ultrapure water and sterilized by filtering, cytokines were added according to table 1 and 2, 10% fetal bovine serum, 100 IU penicillin, 110 μg/ml streptomycin were added and blended.

1640 medium and DMEM medium can also be used for muscle stem cell culturing.

Cytokines were added according to the following tables. All the cytokines in the tables are originated from mouse or human.

TABLE 1

| | Concentration (ng/ml) | | | | | | |
|---|---|---|---|---|---|---|---|
| Component | 1# | 2# | 3# | 4# | 5# | 6# | 7# |
| IFN gamma | 120 | 1 | 10 | 80 | 150 | 100 | 50 |
| IL1 | 50 | 0.5 | 5 | 50 | 100 | 100 | 50 |
| IL2 | 150 | 1 | 10 | 100 | 200 | 150 | 80 |
| IL13 | 80 | 0.5 | 5 | 50 | 100 | 200 | 100 |
| IL-4 | 100 | 2 | 20 | 200 | 400 | 300 | 100 |
| TNFalpha | 150 | 1 | 10 | 100 | 200 | 400 | 200 |

TABLE 2

| | Concentration (ng/ml) | | | | | | |
|---|---|---|---|---|---|---|---|
| Component | 8# | 9# | 10# | 11# | 12# | 13# | 14# |
| GM-CSF | 50 | 0.5 | 5 | 100 | 50 | 10 | 120 |
| sICAM-1 | 50 | 0.5 | 5 | 120 | 50 | 10 | 150 |
| IFN gamma | 120 | 120 | 120 | 120 | 120 | 120 | 120 |
| IL1 | 50 | 50 | 50 | 50 | 50 | 50 | 50 |
| IL-1 alpha receptor | 20 | 1 | 10 | 50 | 100 | 20 | 50 |
| IL-3 | 100 | 2 | 20 | 50 | 200 | 5 | 50 |
| IL2 | 150 | 150 | 150 | 150 | 150 | 150 | 150 |
| IL-10 | 80 | 2 | 20 | 50 | 200 | 5 | 100 |
| IL-16 | 100 | 2 | 20 | 50 | 200 | 5 | 100 |
| IL13 | 80 | 80 | 80 | 80 | 80 | 80 | 80 |
| IL-17 | 120 | 1 | 10 | 20 | 5 | 5 | 150 |
| IP-10 | 40 | 0.5 | 5 | 10 | 1 | 10 | 80 |
| SCYA2 | 60 | 0.5 | 5 | 10 | 2 | 5 | 50 |
| MIG | 50 | 0.5 | 5 | 10 | 2 | 5 | 50 |
| MIP-1 alpha | 100 | 1 | 10 | 20 | 5 | 10 | 200 |
| TGF-beta | 200 | 2 | 20 | 50 | 5 | 20 | 200 |
| IL-4 | 100 | 100 | 100 | 100 | 100 | 100 | 100 |
| TRAF6 | 50 | 0.5 | 5 | 10 | 2 | 5 | 50 |
| FGF | 10 | 0.2 | 2 | 5 | 1 | 2 | 20 |
| IGF | 10 | 0.2 | 2 | 5 | 1 | 2 | 20 |
| PDGF | 10 | 0.2 | 2 | 5 | 1 | 2 | 20 |
| LIF | 20 | 0.2 | 2 | 5 | 1 | 2 | 20 |
| IL-1 alpha | 10 | 0.5 | 5 | 2 | 50 | 2 | 20 |
| mTOR | 20 | 0.2 | 2 | 5 | 1 | 2 | 20 |
| LPS | 10 | 0.1 | 1 | 2 | 1 | 1 | 10 |
| TLR1 | 50 | 0.5 | 5 | 10 | 5 | 10 | 50 |
| IL12 | 40 | 0.4 | 4 | 10 | 5 | 10 | 50 |
| IL23 | 20 | 0.2 | 2 | 5 | 2 | 5 | 20 |
| NGF | 10 | 0.2 | 2 | 5 | 2 | 5 | 20 |
| TNFalpha | 150 | 150 | 150 | 150 | 150 | 150 | 150 |

Example 2. Culture and Detection of Muscle Stem Cell

1) Isolate Muscle Stem Cells

Mouse muscle stem cells: Several 3 day old new born mice were sacrificed, muscles from the limbs were harvested and put into DMEM medium containing 0.2% D-type collagenase, digested at 37° C. for 1.5 hours. The muscle tissues were washed with PBS 3 times after digestion and collected by natural sedimentation for several minutes every time. The collected muscles were triturated by blowing and sucking with Pasteu pipettes and 18 Gauge needles for several times until the muscle tissues were dispersed. The non-muscle impurity was removed by filtrating through a 40 um filter. The filtrate was centrifugated at 1000 rpm for 5 minutes, the pellet was resuspended in F10 medium and seeded in 10 cm dishes, the suspension was transferred to 10 cm dishes covered with 0.05% I-type collagen 3 hours later, 5 ng/ml FGF cytokine was added at the same time, incubated overnight at 37° C. in $CO_2$ incubator. The next day, the muscle cells was digested with trypsin, centrifugated at 1500 rpm for 5 minutes, the cells was washed with PBS twice and resuspended in PBS containing 1.5% BSA, CD34 antibody (BD Pharmingen, cat No: 553733, dilution ratio: 1:20). Integrin $\alpha 7$ (R&D, cat No: FAB3518A, dilution ratio: 1:10) were added, incubated at 37° C. for 45 minutes, centrifugated at 5000 rpm for 5 minutes to collect the cells. The cells were washed with PBS twice. The cells with CD34 and Integrin$\alpha 7$ both positive were selected by Influx flow cytometry. The double positive cells are mouse muscle stem cells.

Human muscle stem cells: Human muscle biopsy was obtained, the non-muscle tissues such as skin, fat and bone were removed with sterile surgery tools. The muscle was cut into small pieces, 3.5 ml dispase II and collagenase D (in equal ratio) per gram of muscle was added, and incubated in 37° C. $CO_2$ incubator for 15 minutes. Triturate the muscle tissues with 5 ml pipette. The above procedure was repeated for 2-3 times until all the muscle tissues have been completely digested. The digestion was stopped by the addition of complete growth medium (2 times of the total volume). The digestion product was filtrated through 100 μm filter; the filtrate was centrifugated at 329 g for 10 minutes. The pellet was resuspended in the complete growth medium in a ration of 3.5 ml medium/g muscle tissue and red cell lysis buffer was added in a volume of 7 times, mixed for several times by turn upside down of the centrifuge tube, filtrated through 40 μm filter, centrifugated at 329 g for 10 minutes to collect the cells. The cells were regulated to a concentration of $0.5-1\times 10^6$ cells/10 ml and seeded in dishes coated with gelatin.

2) Passage of Muscle Stem Cells:

The isolated and purified muscle stem cells were added into the medium prepared in Example 1, respectively, incubated at 37° C. in 5% $CO_2$ incubator. The cells were passaged. once every 48 hours. The passaged cells were cultured at 37° C. in $CO_2$ incubator.

Passage method: The muscle stem cells were washed with 37° C. pre-warmed PBS once when they grown to a density of 70%, trypsin (37° C. pre-warmed) was added, digested for 1-2 minutes, and the reaction was stopped by addition of medium (37° C. pre-warmed). Cells were resuspended, centrifugated at 3000 rpm and room temperature for 6 minutes. The supernatant was discarded and the cell pellet was resuspended in 37° C. pre-warmed medium, diluted 3 times and divided to 3 dishes, incubated at 37° C. in 5% $CO_2$ incubator for 48 hours.

1) Assays:

For every passage of muscle stem cells, immunofluorescent staining was performed to examine the expressing level of molecular marker Pax7 of muscle stem cells.

For every passage of muscle stem cells, in vitro differentiation experiment was performed to examine their differentiation potentials.

Every passage of cells was introduced into the mice muscle induced muscle injury by intramuscular injection to examine their abilities to repair the muscle injury.

Each type of medium could examine forty passages of cells at most.

Immunofluorescent Staining of Muscle Stem Cell Molecular Marker Pax7:

A dish containing passaged cells was obtained, the cells were washed with PBS (phosphate buffer) for 3 times. The cells were fixed with 4% formaldehyde at room temperature for 15 minutes. Washed 3 times with PBS. 1% Tween20 was added, placed at room temperature for 10 minutes. Washed 3 times with PBS. Pax7 antibody (purchased form DSHB) diluted in the PBS containing 1% BSA (Bovine serum albumin) was added, and incubated at room temperature for 1 hour. Wash 3 times with PBS, 5 minutes/time. Fluorescent labeled donkey anti-mouse secondary antibody (1:1000 diluted in the PBS containing 1% BSA) was added, and incubated at room temperature for 1 hour. Washed once with PBS, 2004 DAPI was added, placed at room temperature for 5 minutes. Wash 3 times with PBS, 5 minutes/time. Mounted the slides after the anti quenching agent was added. Observed under Zeiss fluorescence microscope and took pictures.

Cells with fluorescence staining being observed in the nuclear were positive cells. Cells without fluorescence staining being observed in the nuclear were negative cells.

In Vitro Differentiation Assay:

A dish of cultured muscle stem cells was obtained, the cells were washed with PBS pre-warmed at 37° C. for 3 times. DMEM medium containing 2% horse serum wad added, incubated at 37° C. in $CO_2$ incubator for 72 hours. The differentiation efficiency was evaluated under microscopy.

The differentiation potential was considered to be maintained well if >90% of muscle stem cells differentiated to myotubes. The differentiation potential was considered to be maintained partly if a portion of cells differentiated to myotubes. The differentiation potential was considered to be absence if there was no myotube formation.

Muscle Injury Reparation Assay:

Mice model used to induce muscle injury: Wild mice purchased from Charlse River.

A dish of cultured muscle stem cells expressing RFP (Red fluorescent protein) was obtained, washed with 37° C. pre-warmed PBS for one time, digested with 37° C. pre-warmed trypsin for 2 minutes. $1\times 10^{-5}$ muscle stem cells were obtained and resuspended in 200 μl sterile PBS, transferred to a steriled 1 ml syringe, administrated into the gastrocnemius of the injury induced mice without REP expression by intramuscular injection. The cryosections of gastrocnemius were obtained after the mice were nursed for 1 month, stained with laminin to mark the outline of muscle fibers, and stained with DAPI to mark DNA. The sections were observed under laser scanning confocal microscopy to detect the existence of cells expressing RFP in the injury part. The staining method was as the following: Cryosections were washed with PBS for 3 times, fixed with 4% formaldehyde at room temperature for 15 minutes. The sections were washed with PBS for 3 times, 1% Tween 20 was added, incubated at room temperature for 10 minutes.

The sections were washed with PBS for 3 times, laminin antibody (purchased from Abeam) diluted in PBS (containing 1% BSA) was added, incubated at room temperature for 1 hour. The sections were washed with PBS for 3 times, 5 minutes for each time. Fluorescent labeled donkey anti-rabbit secondary antibody diluted in PBS (containing 1% BSA) (1:1000) was added, incubated at room temperature for 1 hour. The sections were washed with PBS for one time. Stain with 20 μM DAPI (4',6-diamidino-2-phenylindole) was added, incubated at room temperature for 5 minutes, washed with PBS for 3 times, 5 minutes for each time. The sections were mounted by addition of quencher. The sections were observed under Zeiss laser scanning confocal microscopy and took pictures.

Detection of more myofibers with red fluorescence in the injury part suggests excellent muscle reparation ability. Detection of a few myofibers with red fluorescence in the injury part suggests weak muscle injury reparation ability. Detection of no myofibers with red fluorescence suggests no muscle reparation ability.

2) Assay Results (1#-14# Indicates F10 Cell Medium Supplemented with Cytokines of Mouse Blood Cells Prepared with the Formulations of Table 1 and Table 2, Respectively):

3)

| Medium formulations | 1st Generation | 5th Generation | 7th Generation | 10th Generation | 15th Generation | 17th Generation | 40th Generation |
|---|---|---|---|---|---|---|---|
| Mouse T cell condition medium | ++/aa/cc | ++/aa/cc | ++/aa/cc | ++/aa/cc | ++/aa/cc | ++/aa/cc | ++/ab/cd |
| Mouse B cell condition medium | ++/aa/cc | — | — | — | — | — | — |
| 1# (MOUSE) | ++/ab/cd | ++/ab/cd | ++/ab/cd | ++/ab/cd | ++/ab/cd | ++/ab/cd | ++/ab/dd |
| 2# (MOUSE) | ++/ab/cd | ++/ab/cd | ++/ab/cd | ++/ab/cd | ++/ab/cd | ++/ab/dd | ++/ab/dd |
| 3# (MOUSE) | ++/aa/cc | ++/aa/cc | ++/aa/cc | ++/aa/cc | ++/aa/cc | ++/aa/cd | ++/ab/dd |
| 4# (MOUSE) | ++/aa/cc | ++/aa/cc | ++/aa/cc | ++/aa/cc | ++/aa/cc | ++/aa/cc | ++/ab/dd |
| 5# (MOUSE) | ++/aa/cc | ++/aa/cc | ++/aa/cc | ++/aa/cc | ++/ab/cd | ++/ab/cd | ++/ab/dd |
| 6# (MOUSE) | ++/aa/cc | ++/aa/cc | ++/aa/cc | ++/ab/cd | ++/ab/cd | ++/ab/cd | ++/ab/dd |
| 7# (MOUSE) | ++/aa/cc | ++/aa/cc | ++/aa/cc | ++/aa/cc | ++/aa/cc | ++/aa/cc | ++/bb/dd |
| 8# (MOUSE) | ++/aa/cc | ++/aa/cc | ++/aa/cc | ++/aa/cc | ++/aa/cc | ++/ab/cd | ++/ab/dd |
| 9# (MOUSE) | ++/aa/cc | ++/aa/cc | ++/aa/cc | ++/aa/cc | ++/aa/cc | ++/ab/cd | ++/ab/dd |
| 10# (MOUSE) | ++/aa/cc | ++/ab/cd | ++/ab/cd | ++/ab/cd | ++/ab/cd | ++/ab/cd | ++/ab/dd |
| 11# (MOUSE) | ++/aa/cc | ++/aa/cc | ++/aa/cc | ++/aa/cc | ++/aa/cc | ++/ab/cd | ++/ab/dd |
| 12# (MOUSE) | ++/aa/cc | ++/ab/cd | ++/ab/cd | ++/ab/cd | ++/ab/cd | ++/ab/cd | ++/ab/dd |
| 13# (MOUSE) | ++/aa/cc | ++/ab/cd | ++/ab/cd | ++/ab/cd | ++/ab/cd | ++/ab/cd | ++/ab/dd |
| 14# (MOUSE) | ++/aa/cc | ++/aa/cc | ++/aa/cc | ++/aa/cc | ++/ab/cd | ++/ab/cd | ++/ab/dd |

++: Positive for Pax7 Immunofluorescent staining;
+: Weakly positive for Pax7 Immunofluorescent staining;
−: Negative for Pax7 Immunofluorescent staining
aa: Maintain full potential of differentiation;
ab: Maintain partial potential of differentiation;
bb: No differentiation potential.
cc: Excellent muscle injury reparation ability;
cd: weak muscle injury reparation ability;
dd: No muscle injury reparation ability.
—: had not been detected.

The pictures for part of the assay results were indicated in the attached figures.

5. Analysis of Results

The results described above indicate that all the muscle cells cultured for 40 passages were Pax7 positive after staining with Pax7. The cells of each passage could express muscle stem cell molecular marker Pax7 and differentiate to mature myotubes. All the muscle stem cells from passage 1-30 were able to repair muscle injury. At present, all the muscle stem cells up to passage 18 being detected were able to take part in the repair of muscle injury in mouse in vivo.

The above examples are disclosed for illustrating of the embodiments of this invention and could not be considered to limit the scope of this invention. Furthermore, without departing from the scope and spirit of this invention, various amendments and variety of methods and compositions described in this invention are obvious to the skilled in the art. Although the invention is described in detail with various specific preferred examples, it should be understood that the invention is not limited by these specific examples. In fact, various amendments as illustrated above is obvious to the skilled in the art to arrive this invention, they should be included in the scope of this invention.

The invention claimed is:

1. A medium for culturing muscle stem cells, wherein the medium is a cell culture medium comprising a basal culture medium supplemented with cytokines secreted by blood cells or conditional medium of blood cells comprising cytokines, and wherein said cytokines comprise IL1, IL4, IL13, TNF alpha, IL2 and IFN gamma; and concentration of any individual cytokine supplemented to said cell culture medium is greater than 0.5 ng/ml;
   wherein the basal culture medium is selected from the group consisting of DMEM, RPMI 1640, MEM, DEME/F12, F10 medium, CD293 medium, medium 231, and medium 106; and
   wherein all the cytokines or the blood cells used to prepare said conditional medium are from the same species as the muscle stem cells to be cultured.

2. The medium for culturing muscle stem cells of claim 1, wherein said blood cell conditional medium is lymphocyte conditional medium.

3. The medium for culturing muscle stem cells of claim 1, wherein said blood cell conditional medium is B cell conditional medium or T cell conditional medium.

4. The medium for culturing muscle stem cells of claim 1, further comprising one or more cytokines secreted by blood cells selected from the group consisting of GM-CSF, sICAM-1, IL-1 alpha receptor, IL1 alpha, IL-3, IL-10, IL-16, IL-17, IP-10, SCYA2, MJG, MIP-1 alpha, TGF-beta, TRAF6, FGF, IGF, PDGF, LIF, mTOR, LPS, TLR1, IL12, IL23, NGF, and IL1 beta.

5. The medium for culturing muscle stem cells of claim 1, wherein total concentration of cytokines supplemented to said cell culture medium is not less than 6 ng/ml.

\* \* \* \* \*